US009958389B2

(12) United States Patent
Nuutinen et al.

(10) Patent No.: US 9,958,389 B2
(45) Date of Patent: *May 1, 2018

(54) METHOD FOR DETERMINING A SCALE INHIBITOR CONCENTRATION IN A SAMPLE

(71) Applicant: Kemira Oyj, Helsinki (FI)

(72) Inventors: Vesa Nuutinen, Helsinki (FI); Susanna Toivonen, Espoo (FI); James Johnstone, Banchory (GB); Harri Härmä, Turku (FI); Paul Mundill, Espoo (FI)

(73) Assignee: KEMIRA OYJ, Helsinki (FI)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/037,680

(22) PCT Filed: Nov. 18, 2014

(86) PCT No.: PCT/FI2014/050877
§ 371 (c)(1),
(2) Date: May 19, 2016

(87) PCT Pub. No.: WO2015/075308
PCT Pub. Date: May 28, 2015

(65) Prior Publication Data
US 2016/0290923 A1 Oct. 6, 2016

(30) Foreign Application Priority Data
Nov. 19, 2013 (FI) .................... 20136151

(51) Int. Cl.
G01N 21/64 (2006.01)
G01N 21/77 (2006.01)
G01N 1/34 (2006.01)
G01N 1/38 (2006.01)

(52) U.S. Cl.
CPC .......... *G01N 21/6408* (2013.01); *G01N 1/34* (2013.01); *G01N 1/38* (2013.01); *G01N 21/77* (2013.01); *G01N 2021/6419* (2013.01); *G01N 2021/6421* (2013.01); *G01N 2021/7786* (2013.01)

(58) Field of Classification Search
CPC .......... G01N 21/64; G01N 1/34; G01N 21/77; G01N 1/38
USPC .................... 436/104, 111, 129, 172
See application file for complete search history.

(56) References Cited

U.S. PATENT DOCUMENTS 3,962,110 A 6/1976 Tate
4,808,541 A * 2/1989 Mikola ................ C07F 9/3817
435/968
5,389,548 A 2/1995 Hoots et al.
6,312,644 B1 11/2001 Moriarty et al.
6,329,205 B1 12/2001 Diwu et al.
6,344,360 B1 * 2/2002 Colvin .................... C07F 5/025
436/166
2004/0135125 A1 7/2004 Morris et al.
2012/0032093 A1 2/2012 Moore et al.
2016/0290924 A1 * 10/2016 Nuutinen ............ G01N 21/6408
2017/0002629 A1 * 1/2017 Hurtevent .............. C09K 8/528

FOREIGN PATENT DOCUMENTS

| EP | 0094822 A1 | 11/1983 |
| JP | 2000356596 A | 12/2000 |
| WO | 2005000747 A2 | 1/2005 |
| WO | 2012098186 A1 | 7/2012 |

OTHER PUBLICATIONS

Li, M. et al. Journal of the American Chemical Society 1995, 117, 8132-8138.*
Comby, S. et al, Inorganic Chemistry 2004, 43, 7369-7379.*
Harte, A. J. et al, Inorganic Chemistry 2006, 45, 9465-9474.*
Plush, S. E. et al, Organic Letters 2007, 9, 1919-1922.*
Hänninen, P. E et al, Fuzzy Liquid Analysis by an Array of Nonspecifically Interacting Reagents: The Taste of Fluorescence. Journal of the American Chemical Society, May 2013, vol. 135, No. 20, pp. 7422-7425.
Kogej, K. et al. Understanding the interaction between trivalent lanthanide ions and stereoregular polymethacrylates through luminescence, binding isotherms, NMR, and interaction with cetylpyridinium chloride. Langmuir, Nov. 2013, vol. 29, No. 47, pp. 14429-14437. Available from the internet Oct. 31, 2013.
Kido, J. et al. Effect of ultrasonic irradiation on luminescence properties of lanthanide-polyelectrolyte complexes. Polymer, 1992, vol. 33, No. 11, pp. 2273-2276.
Georges, J. Lanthanide-sensitized luminescence and applications to the determination of organic analytes. A review. Analyst, Dec. 1993, vol. 118, No. 12, pp. 1481-1486.
Poynton N. et al., Development of a New Tagged Polymeric Scale Inhibitor with Accurate Low-Level Residual Inhibitor Detection, for Squeeze Applications, SPE International Conference on Oilfield Scale, May 30, 2012, XP55135347.

(Continued)

Primary Examiner — Arlen Soderquist
(74) Attorney, Agent, or Firm — Berggren LLP

(57) ABSTRACT

The invention relates to a method for determining a scale inhibitor concentration in a sample comprising at least a first scale inhibitor, which is a synthetic organic compound comprising at least one ionized group. The method comprises optionally diluting and/or purifying theسample, and allowing the sample to interact with a reagent comprising a lanthanide(III) ion. The sample is excited at a first excitation wavelength and a sample signal deriving from the lanthanide (III) ion is detected at a signal wavelength by using time-resolved luminescence measurement, and the concentration of the at least first scale inhibitor in the sample is determined by using the detected sample signal.

18 Claims, 1 Drawing Sheet

(56) References Cited

OTHER PUBLICATIONS

Search report of FI20136151, Finnish Patent and Registration Office, dated Jun. 19, 2014.
International Search Report PCT/FI2014/050877, issued by the European Patent Office, dated Feb. 17, 2015.

* cited by examiner

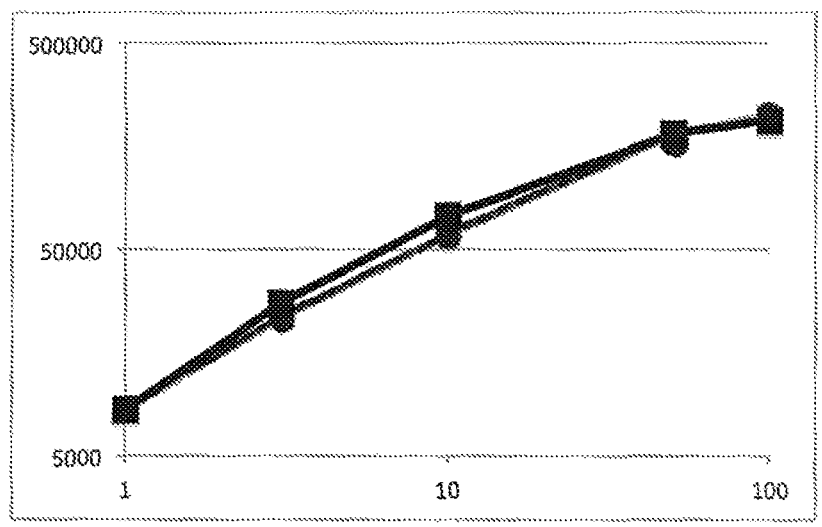

METHOD FOR DETERMINING A SCALE INHIBITOR CONCENTRATION IN A SAMPLE

PRIORITY

This application is a U.S national application of the international application number PCT/FI2014/050877 filed on Nov. 18, 2014 and claiming priority of Finnish national application FI20136151 filed on Nov. 19, 2013, the contents of both of which are incorporated herein by reference.

The present invention relates to a method for determining a scale inhibitor concentration in a sample according to the preambles of the enclosed independent claims.

Scale inhibitors are used, for example, in offshore oil production for stimulation of the oil wells, for controlling and/or preventing scale depositions. A scale inhibitor may be injected continuously into an oil well, or it may be periodically injected if a so-called squeeze treatment is employed. In the squeeze treatment a scale inhibitor pulse is injected into the oil well and the scale inhibitor leaches back into the produced fluids. The concentration of the scale inhibitor in the produced fluids should be sufficiently high in order to avoid scale formation or precipitation. The concentration of scale inhibitor normally decreases exponentially after the initial injection, and when the concentration has fallen below a predetermined value the squeeze treatment of the oil well is repeated. Consequently, it is important to obtain reliable knowledge about the concentration of the scale inhibitor in the produced fluids for securing well-timed squeezing treatment. If the squeezing treatment is performed too late, harmful scales may be formed and disturb the production process.

Nowadays different analytical techniques are used for determining the scale inhibitor concentration in the produced fluids. Examples of used techniques are inductively coupled plasma (IPC), high-performance liquid chromatography (HPLC) and liquid chromatography-mass spectrometry (LC-MS). However, there is a continuous need for new, accurate and simple analysis methods.

It is an object of the present invention to reduce or even eliminate the problems appearing in prior art.

An object of the invention is to provide a simple and reliable method for determining the amount of scale inhibitor in a sample, especially in an oilfield sample.

Another object of the present invention is to provide a fast method for determining at least one scale inhibitor in a sample.

In order to realise the above-mentioned objects, among others, the invention is characterised by what is presented in the characterising parts of the enclosed independent claims.

Some preferred embodiments according to the invention are disclosed in the dependent claims presented further below.

Typical method according to the present invention for determining a scale inhibitor concentration in a liquid sample comprising at least a first scale inhibitor, which is a synthetic organic compound comprising at least one ionised group, comprises
- optionally diluting and/or purifying the sample,
- allowing the sample to interact with a reagent comprising a lanthanide(III) ion,
- exciting the sample at a first excitation wavelength and detecting a sample signal deriving from the lanthanide (III) ion at a signal wavelength by using time-resolved luminescence measurement, and
- determining the concentration of the at least first scale inhibitor in the sample by using the detected sample signal.

The method according to the present invention is suitable for determining concentration of scale inhibitor in any industrial water system or industrial water system sample. These industrial water systems where scale inhibitors may be employed include, but are not limited to, cooling tower water systems including open, recirculating, closed and once-through systems; petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurisation water; water reclamation and purification systems; membrane filtration water systems; food processing streams, such as meat, vegetable, sugar beets, sugar cane, grain, poultry, fruit and soybean processing streams; and waste treatment systems as well as in clarifiers, liquid-solid applications, municipal sewage treatment and industrial or municipal water systems. Preferably the method is used for determining a concentration of at least one scale inhibitor in a sample originating from petroleum wells, downhole formations, geothermal wells and other oil field applications. While some of the exemplary methods are described herein in relation to a sample originating from an oilfield or an oil well or from an oil production process, it will be understood that the methods may be adapted for use with other such samples and/or systems.

Now it has been surprisingly found out that by using the exemplary methods described herein the time-resolved luminescence signal derived from an interacted reagent comprising a lanthanide(III) ion, such as europium, excited at a suitable first wavelength, correlates accurately to the scale inhibitor concentration in a sample. This method may be utilised for determining the presence and/or concentration of a scale inhibitor in the sample and it can detect even low scale inhibitor concentration in a sample, such as an oilfield sample. Significant reduction in the detection limit of scale inhibitor concentrations may be achieved by using time-resolved luminescence signal of a lanthanide(III) ion. The detected sample signal normally increases in the presence of a first scale inhibitor and correlates to the concentration of the first scale inhibitor in the sample. A further advantage is that the method according to the invention is simple and fast to perform.

As used herein the term "scale inhibitor" is used in its ordinary sense as understood by one skilled in the art, and thus may be used herein to refer to or describe synthetic chemical compositions or synthetic organic compounds, which comprise at least one ionised group, and which, when added to an aqueous system that tends to form scale, reduce, control, disperse or inhibit the formation, deposition and/or adherence of scale deposits on substrate surfaces in contact with a scale-forming aqueous system. In the context of the exemplary embodiments the term "scale inhibitor" denotes a synthetic organic compound or substance, preferably a synthetic polymer or copolymer.

As used herein the term "polymer" is used to denote a synthetic substance which is composed of a number of repeating monomer units, same or different, joined together to form a polymer backbone. A polymer is formed of at least two, preferably a plurality of monomers. As used herein the term "copolymer" is used to denote a polymer which comprises two or more different monomer units. The type of the copolymer depends on the arrangement of the different monomer units in its structure. The copolymer may be alternating, random, block or graft copolymer.

The sample, which comprises at least a first scale inhibitor, is a liquid sample.

According to one exemplary embodiment scale inhibitor comprises at least one, preferably two or more ionised groups, more preferably at least three ionised groups, even more preferably at least four ionised groups, attached to the scale inhibitor compound structure or polymer/copolymer backbone. According to another exemplary embodiment scale inhibitor comprises one or two ionised groups, per at least some of the monomer units of the scale inhibitor polymer/copolymer. It is not necessary that all monomer units comprise ionised groups. The ionised groups may be selected from phosphates, phosphonates, carboxylates, sulphonates and/or amines, preferably from carboxylates, sulphonates and/or amines. Amines may be primary amines, secondary amines, tertiary amines and/or quaternary amines. Phosphates may be primary phosphates or secondary phosphates. In case the scale inhibitor comprises two or more ionised groups, the ionised groups in the scale inhibitor may all be similar to each other or they may be different from each other. The scale inhibitor may be anionic, cationic or zwitterionic, preferably anionic.

In exemplary embodiments one or more of the ionised groups of the scale inhibitor are capable of interacting with the reagents comprising lanthanide(III) ions. In this context the term "interact" means that the ionised groups can react, coordinate and/or chelate with the reagents comprising lanthanide(III) ions. Especially, the ionised groups of the scale inhibitor can react, coordinate and/or chelate with the lanthanide(III) ions.

According to various embodiments of the invention the scale inhibitor is selected from group comprising polyelectrolyte compounds comprising carboxylate and/or phosphonate groups; homopolymers and copolymers of ethylenically unsaturated acid monomers; organophosphonates; and combinations thereof. The polyelectrolyte compounds may comprise a multiplicity of interactive groups, which can be ionised, for example, carboxylate and/or phosphonate groups. The scale inhibitor may be, for example, a polycarboxylic acid, such as polyacrylic acid, polymethacrylic acid, polymaleic acid or any of their salts with monovalent cations. Alternatively the scale inhibitor may be, for example, maleic anhydride. The scale inhibitor may be a homopolymer or a copolymer of an alpha, beta-ethylenically unsaturated acid monomer such as acrylic acid or methacrylic acid, a diacid such as maleic acid or maleic anhydride, itaconic acid, fumaric acid, monoesters of diacids with alkanols having 1-8 carbon atoms, and/or mixtures thereof. In case the scale inhibitor is a copolymer, it may be composed of two or more co-monomers, and the first -co-monomer may be any alpha, beta-ethylenically unsaturated monomer and the second co-monomer may be a non-polar group or monomer, such as styrene or olefinic monomer; or a polar functional group or monomer, such as vinyl acetate, vinyl chloride, vinyl alcohol, an alkyl acrylate, vinyl pyridine, vinyl pyrrolidone, acrylamide or an acrylamide derivative, etc.; or an ionic functional group or monomer, such as styrenesulfonic acid, 2-acrylamido-2-methylpropanesulfonic acid (AMPS), vinylsulfonic acid or vinylphosphonic acid. The scale inhibitor may be an organophosphonate, such as amino tris(methylene phosphonic acid), 1-hydroxy ethylidene-1,1-diphosphonic acid, diethylenetriamine penta(methylene phosphonic acid) or phosphonobutane-tricarboxylic acid.

The scale inhibitor may have any necessary or desired molecular weight. For example, in an exemplary embodiment, the scale inhibitor may have a molecular weight of from about 500 to about 100 000 Daltons, preferably 500 to 100 000 Daltons, more preferably 500-30 000 Daltons, even more preferably 1000-12 000 Daltons.

In exemplary embodiments, the dosing or concentration of the scale inhibitor to an aqueous system will be an amount sufficient to produce a desired reduction, control, or inhibition result. In each system, the scale inhibitor may have a predetermined set point, e.g. amount or range, to achieve a desired effect. The exemplary methods can be used to detect the concentration of the scale inhibitor in the system, so that the predetermined set point amount or range can be achieved and/or maintained. For example, the concentration of the scale inhibitor in a liquid sample, originating for example from an oilfield, oil well or from an oil production process, is sometimes in the range of 0.5-200 ppm, preferably 1-50 ppm, more preferably 1-10 ppm. The sensitivity of the method may be selected so that it can detect the concentration of a scale inhibitor within the effective amount or range. For example, the method may be configured to directly detect or measure the concentration of the scale inhibitor in the liquid sample within this range. Alternatively, additional steps may be taken to adapt the method or modify the sample, e.g., with optional purification and/or dilution steps, so that the concentration of the scale inhibitor therein falls within the detection limits of the method.

According to one embodiment of the invention, one or more of the scale inhibitors in a sample interact with a reagent comprising lanthanide(III) ion, and the resulting interaction product(s) is(are) detected using a time-resolved luminescence technique. An exemplary lanthanide(III) ion is selected from europium, terbium, samarium or dysprosium ions, preferably from europium ion or terbium ion. Even more preferably the lanthanide(III) ion is europium ion. Exemplary reagents comprising a lanthanide(III) ion may be a lanthanide(III) salt, such as $EuCl_3$ or $TbCl_3$, or a luminescent lanthanide chelate, such as {2,2',2'',2'''-[(4'-phenyl-2,2': 6'-2''-terpyridine-6,6''-diyl)bis(methylenenitrilo)]tetrakis (acetato)}europium(III) or 2,2',2'',2'''[[4-[(4-phenyl) ethynyl]pyridine-2,6-diyl]bis(methylenenitrilo)]tetrakis-(acetato)europium(III). Preferably, the reagent comprising a lanthanide(III) ion is a lanthanide(III) salt, such as $EuCl_3$ or $TbCl_3$, more preferably europium(III) salt, such as $EuCl_3$.

According to another embodiment of the invention it is also possible to use a combination of different reagents with same or different lanthanide(III) ions. For example, if the sample comprises a plurality of different scale inhibitors which have different affinity to different reagents and/or lanthanide(III) ions, it is possible to determine the concentration of the first scale inhibitor by using a sample signal from a first reagent having a lanthanide(III) ion and the concentration of the second scale inhibitor by using a sample signal from a different second reagent having a lanthanide (III) ion.

According to an embodiment it is possible to use a low amount of lanthanide(III) ion for determining the scale inhibitor concentration in the sample. According to one embodiment the concentration of the lanthanide(III) ion in the sample may be in the range of 0.01-10 mM, preferably 0.01-1 mM, more preferably 0.01 mM-0.1 mM, even more preferably about 0.01 mM. The lanthanide(III) ion concentration is given for the final sample volume for which the time-resolved luminescence measurement is performed.

According to the various embodiments, time-resolved luminescence measurement can be used to measure the concentration of an individual scale inhibitor, or a plurality thereof, in a liquid sample, and/or to measure the combined total concentration of a plurality of scale inhibitors. In embodiments in which an individual scale inhibitor concentration is being determined, the reagent comprising lanthanide(III) ion may be configured to preferentially interact with the selected individual scale inhibitor being measured, and the interaction product is detected using time-resolved luminescence measurement. In embodiments in which a combined total concentration of a plurality of scale inhibitors is being determined, the reagent comprising lanthanide (III) ion may be configured to interact with all of the plurality of scale inhibitors, and the combined interaction products are detected using time-resolved luminescence measurement.

Preferably the time-resolved luminescence measurement is time-resolved fluorescence measurement. In time-resolved fluorescence, the sample containing the interaction product(s) of one or more scale inhibitor(s) and one or more reagent(s) comprising lanthanide(III) ion is excited at an excitation wavelength and the fluorescence sample signal is detected at an emission signal wavelength. An exemplary gate time between the excitation and emission may be, for example 0.5-800 μs, preferably 1-500 μs. The emission signal wavelength is typically longer than the excitation wavelength.

Excitation wavelength, which is used in the present method, may be selected or determined by studying the excitation maximum in the excitation spectrum of the formed interaction product of the first scale inhibitor and the reagent comprising lanthanide(III) ion. For example, the excitation wavelength may be in the range of 200-400 nm and the emission signal wavelength for the sample signal may be about 500-650 nm. For example, the excitation wavelength for europium is 340 nm and the optimum emission signal wavelength 615 nm. Correspondingly, the excitation wavelength for terbium is 254 nm and the optimum emission signal wavelength 545 nm. The excitation spectrum for the interaction product of the scale inhibitor and reagent comprising lanthanide(III) ion may be measured prior to starting the determination protocol or the excitation spectrum may be obtained or estimated from the literature.

It is also possible that the sample further comprises a second scale inhibitor, optionally a plurality of successive scale inhibitors, and the method may be used to determine individual concentrations of each scale inhibitor in the sample. The concentration of a second scale inhibitor or any successive scale inhibitor in the presence of the first scale inhibitor may be determined by using time-resolved luminescence or any other suitable analytical technique.

According to one embodiment of the invention the concentration of a first scale inhibitor is determined by exciting the sample at a first excitation wavelength and detecting a first sample signal deriving from the lanthanide(III) ion by using time-resolved luminescence measurement, and the concentration of the second scale inhibitor is determined by exciting the sample at a second excitation wavelength and detecting a second sample signal deriving from the lanthanide(III) ion by using time-resolved luminescence measurement. The individual excitation spectrum for each respective interacted scale inhibitor and lanthanide(III) ion may be measured prior to starting the measurement or the individual excitation spectra may be obtained or estimated from the literature. For example, the first excitation wavelength may be substantially the excitation maximum of the first scale inhibitor in the presence of the reagent comprising lanthanide(III) ion, and the second excitation wavelength may be substantially the excitation maximum of the second scale inhibitor in the presence of the reagent comprising lanthanide(III) ion. The reagents for determining the first and the second scale inhibitor may be the same or different. The reagents may, for example, comprise different lanthanide(III) ions.

If time-resolved luminescence is being used to measure a plurality of interaction products within a sample, the method may be configured in order to better distinguish the interaction product signals from each other. For example, it is possible to use different excitation wavelengths, different reagents comprising different lanthanide(III) ions, and/or different signal modifiers, respectively, with one or more of the interaction products, to help to distinguish the signals resulting from such interaction products.

In case two or more scale inhibitors are detected by using reagent(s) comprising lanthanide(III) ions and time-resolved luminescence measurement, it may be desirable to have a measurable difference between the excitation wavelengths of the first and second and optionally any successive interaction products of scale inhibitors and reagent(s). For example, the difference between the first excitation wavelength and second excitation wavelength, and optionally any successive excitation wavelength, is at least 10 nm, preferably at least 20 nm, more preferably at least 25 nm. Depending on the sensitivity of the measurement device, a greater difference between the excitation wavelengths may make it easier to distinguish the detected sample signals corresponding to the respective scale inhibitor concentrations in the sample. According to one embodiment of the invention the sample comprises three or more different scale inhibitors and the excitation is performed at three or more excitation wavelengths, respectively. Each excitation wavelength may be chosen according to the excitation maximum of each interacted scale inhibitor which is being determined.

According to one embodiment of the invention a signal modifier, which comprises a metal ion, may be added to the sample before the excitation of the sample. The signal modifier may be used to modify the sample signal, e.g. its intensity, or to modify the difference between excitation wavelengths for different scale inhibitors. An exemplary signal modifier may comprise a metal ion which is selected from a group comprising copper, nickel, chromium, iron, gold, silver, cobalt, and any of their mixtures. Preferably the signal modifier comprises copper(II). It may also possible to modify the effect of the sample matrix to the sample signal by using a signal modifier.

The concentration of a second scale inhibitor, or any successive scale inhibitor, may alternatively be determined by using any suitable analytical technique or detection method. Exemplary methods include, for example, luminescence, time-resolved luminescence, direct fluorescence, absorbance, spectrophotometry, optical rotation measurement, photon counting, inductively coupled plasma (IPC), high-performance liquid chromatography (HPLC), liquid chromatography-mass spectrometry (LC-MS), size exclusion chromatography, colorimetric methods, NMR, or a combination thereof. For determining individual concentrations for a plurality of different scale inhibitors, respectively, in one sample any possible combination of the said analytical techniques or detection methods may be used. For example, in a sample comprising three scale inhibitors the concentrations of the first and second scale inhibitors may be determined by using reagents comprising lanthanide(III) ions and time-resolved luminescence measurement and the concentration of the third scale inhibitor may be determined by using another spectroscopic measurement method. Alternatively, one of the scale inhibitors may be tagged with a fluorescence tag, such as fluorescein, and the individual concentration of that tagged scale inhibitor may be determined with direct fluorescence detection of the tag.

In exemplary embodiments, the sample may be pre-treated before the concentration of the scale inhibitor is measured. According to one embodiment of the invention the sample may be purified before the addition of and/or interaction with the reagent comprising lanthanide(III) ion for removal of disturbing or interfering substances and/or compounds. For example, pre-cleaning may help to minimise the background noise caused by the components of a liquid sample, e.g. water, system. Exemplary purification methods include, e.g., centrifugation, size exclusion chromatography, cleaning with solid-phase extraction (SPE) cartridges, dialysis techniques, extraction methods for removing hydrocarbons, filtration, microfiltration, ultrafiltration, nanofiltration, membrane centrifugation, and/or other methods used to separate the polymeric species from smaller compounds, for example other treatment chemicals or salts. In an embodiment, salt concentration of the sample may be reduced or insoluble particles may be removed before addition of the reagent comprising lanthanide(III) ion and the time-resolved luminescence measurement. In another exemplary embodiment, salt concentration of the sample may be reduced before addition of the reagent comprising lanthanide(III) ion and the performance of the time-resolved luminescence measurement. In another exemplary embodiment, if the initial concentration of the scale inhibitor in the sample is high, e.g. outside of the detection limits of the method, the sample may be diluted before addition and/or interaction with the reagent comprising lanthanide(III) ion. Possible diluents are water, one or more aqueous buffer solutions, or any of their mixtures. In exemplary embodiments, one or more of the above pretreatment steps may be performed on a sample before measurement of scale inhibitor concentration. For example, before measurement the sample may be either purified or diluted, or the sample may be both purified and diluted.

In exemplary embodiments, one or more buffers may be added to the sample prior to the measurement, to improve the signal-to-noise and signal-to-background ratio of the detected sample signals. Examples of these buffers include, for example, those comprising sulfonic acid derivatives, such as e.g. HEPES (2-[4-(2-hydroxyethyl)piperazin-1-yl]ethanesulfonic acid, $pK_a$ 7.48), PIPES (1,4-piperazinediethanesulfonic acid, $pK_a$ 6.76), MOPS (3-morpholinopropane-1-sulfonic acid, $pK_a$ 7.2) and MES (2-(N-morpholino)ethanesulfonic acid, $pK_a$ 6.15), HEPES being preferred. Further, one preferred buffer is TRIS (2-Amino-2-hydroxymethyl-propane-1,3-diol), especially used as a mixture with a buffer comprising sulfonic acid derivative, such as HEPES.

According to one embodiment the pH value of the sample is adjusted to a suitable level, for example, in the range between pH 3 and pH 8, preferably in the range from pH 5 to pH 8. Any suitable buffer that does not significantly disturb the detection of sample signal, may be used. Exemplary buffers are given above, but other buffers may also be used.

The methods described herein may be automatized or they may be performed manually. According to one embodiment the method is performed as on-line measurement. In an exemplary embodiment, the measurement is preferably used on-site, such as at an offshore oil platform and provides almost instant information about on-going production. In some embodiments, the measurement time is relatively fast, so that for example the total measurement time for analysing one sample from optional purification to obtaining the scale inhibitor concentration value may be less than 15 minutes, preferably less than 10 minutes.

The analysis of the scale inhibitor concentrations according to the present invention may be performed in any suitable detection or fluid vessel. The fluid vessel may be e.g. a well, a part of a fluidic device, microfluidic chip or a cuvette. The fluid vessel may be selected to provide a predetermined amount of sample fluid for measurement. For example, according to one embodiment of the invention a fixed volume of the sample is added to a first fluid vessel, such as cuvette, comprising a reagent comprising lanthanide(III) ions. The first scale inhibitor in the sample is allowed to interact with the reagent comprising lanthanide(III) ions in the first fluid vessel, and the sample is excited at the first excitation wavelength and the time-resolved fluorescence signal is detected at the signal wavelength.

In case it is desirable to further measure the concentration of a second scale inhibitor or any successive scale inhibitor that is in the same sample, the determination may be performed separately, e.g. in parallel or series, by using a plurality of fluid vessels. For example, a predetermined number of fluid vessels may be selected, corresponding to the number of scale inhibitors to be determined. Each fluid vessel may be independently configured to determine a respective scale inhibitor. The same or different detection method may be used in each fluid vessel, depending for example on the nature of the scale inhibitor.

For example, according to one embodiment of the invention, the sample may comprise two or more scale inhibitors, each of which may be measured according to time-resolved fluorescence. The measurement apparatus may contain a plurality of fluid vessels, and each fluid vessel may independently comprise a reagent comprising lanthanide(III) ion, that is selected for the respective scale inhibitor to be determined in such vessel. A fixed volume of the sample may be introduced to each fluid vessel, and the scale inhibitors may be allowed to interact with the reagents in the respective fluid vessels. In each vessel the sample is excited at an excitation wavelength and the time-resolved fluorescence signal is detected at the signal wavelength. As a result, each fluid vessel may provide information related to the concentration of a different scale inhibitor in the sample.

In embodiments in which a plurality of fluid vessels are used, the reagent comprising lanthanide(III) may be the same or different in the different fluid vessels. The excitation wavelength of the sample in the second fluid vessel or successive fluid vessels may be different than the excitation wavelength of the sample in the first fluid vessel.

For example, according to another embodiment the sample comprises a first scale inhibitor and a second scale inhibitor, and the concentration of each is determined, respectively, in first and second fluid vessels. In the first fluid vessel, the first scale inhibitor is allowed to interact with a known amount of a reagent comprising, for example, terbium(III) ion. In the second vessel the second scale inhibitor is allowed to interact with a known amount of a reagent comprising, for example, europium(III) ion. The individual concentrations of the first and the second scale inhibitors are determined on basis of the measured time-resolved fluorescence sample signals of terbium and europium reacted with the first and second scale inhibitor, respectively.

According to another embodiment of the invention the sample may comprise first, second and third scale inhibitors, of which the third scale inhibitor is tagged with a chromophore. A fixed volume of the sample is added to three fluid vessels. The first and second vessels comprise reagents with lanthanide(III) ions. In the first fluid vessel the first scale inhibitor is allowed to interact with a first reagent comprising lanthanide(III) ion, the sample is excited at the first excitation wavelength, which is specific for the first scale inhibitor and the time-resolved fluorescence signal is detected at the signal wavelength, the first sample signal corresponding to the concentration of the first scale inhibitor. In the second fluid vessel the second scale inhibitor is allowed to interact with a second reagent comprising lanthanide(III) ion, the sample is excited at the second excitation wavelength, which is specific for the second scale inhibitor and the time-resolved fluorescence signal is detected at the signal wavelength, the second sample signal corresponding to the concentration of the second scale inhibitor. In the third fluid vessel the concentration of the third scale inhibitor is obtained by measurement of the inherent absorbance of the sample. Since only the third scale inhibitor comprises a chromophore, the measured absorbance is proportional to the concentration of the third scale inhibitor in the sample. In case the third scale inhibitor is tagged with a fluorescent tag, the determination of the concentration of the third scale inhibitor may be performed on basis of a direct fluorescence signal of the tag. Using the results obtained from the three fluid vessels, one may determine the respective concentrations of the first, second, and third scale inhibitors in the sample.

According to another embodiment of the invention the method may be performed in a single fluid vessel, even if the sample comprises a plurality of scale inhibitors. For example, the sample may comprise a first, a second and a third scale inhibitor, of which the third scale inhibitor is tagged with a fluorophore. A fixed volume of the sample is added to a fluid vessel, e.g. cuvette, comprising a reagent comprising lanthanide(III) ions and the scale inhibitors are allowed to interact with the reagent comprising lanthanide (III) ions. The concentration of the first scale inhibitor in the sample is obtained when the sample is excited at the first excitation wavelength specific for the first scale inhibitor and the time-resolved fluorescence sample signal is detected at the signal wavelength, this first sample signal corresponding to the concentration of the first scale inhibitor. The concentration of the second scale inhibitor is obtained when the sample is excited at the second excitation wavelength, which is specific for the second scale inhibitor and the second time-resolved fluorescence sample signal is detected at the signal wavelength, this second sample signal corresponding to the concentration of the second scale inhibitor. The concentration of the third scale inhibitor is obtained by direct measurement of the specific fluorescence signal of the fluorophore.

According to one embodiment of the invention the sample comprises two or more scale inhibitors, whereby the detected sample signal deriving from the lanthanide(III) ion at the signal wavelength by using time-resolved luminescence measurement corresponds to the total concentration of the two or more scale inhibitors in the sample. In this case the sample comprises a plurality of scale inhibitors, which absorb excitation energy at the same wavelength, and the sample signal, in fact, correlates with the total concentration of all scale inhibitors in the sample, which are excited at the same wavelength.

The method according to the invention is quantitative, i.e. the signals which are obtained for the sample or for first, second or each successive scale inhibitor, correspond to the total concentration of all scale inhibitors or to the individual concentrations first, second or each successive scale inhibitor.

For determining the concentration of a scale inhibitor, a standard curve or standard point may be prepared before performing the determination method. The concentration of the scale inhibitor may be calculated on basis of the obtained sample signal by using the predetermined standard curve or the standard point. Alternatively the measurement instrument may be pre-calibrated. In case the sample comprises a plurality of scale inhibitors, a standard curve or standard point may be prepared for each scale inhibitor to be determined.

EXPERIMENTAL

Some embodiments of the invention are described more closely in the following non-limiting examples.

Examples employ scale inhibitor polymers, which are sulphonated polycarboxylates, i.e. copolymers comprising allylsulphonate- and maleic anhydride based monomers in 50/50 molar ratio. The molecular weight of the copolymers is between 1500 and 12 000 Da. In the examples, the following scale inhibitor polymers, given in Table 1, are referenced.

TABLE 1

Scale inhibitor polymers of Examples 1 and 2

| Polymer | Description |
| --- | --- |
| P1 | Sulphonated polycarboxylate |
| P2 | Sulphonated polycarboxylate with a fluorescent moiety |
| P40 | Sulphonated polycarboxylate with a phosphorous moiety |

Example 1

Concentration of a scale inhibitor polymer is measured in the Example 1.

First, 1450 µL of artificial brine solution comprising 600 mM NaCl, 7 mM $MgCl_2*6H_2O$, 15 mM $CaCl_2*2H_2O$, 3 mM KCl and 0.5 mM $BaCl_2$, in filtrated and deionized (MilliQ) water was added to a cuvette (Fischer brand Macro cuvette, Polystyrene, FB55143). Thereafter, 250 µL of 10 µM of $EuCl_3$ in a 5 mM 4-(2-hydroxyethyl)-1-piperazineethanesulfonic acid (HEPES)-NaOH buffer, pH 7.6, and 800 µL of artificial brine solution as above containing varying concentrations of scale inhibitor polymer was added to the cuvette. The time-resolved luminescence signal was measured with a luminescence reader (Aqsens Oy, Turku, Finland) using excitation wavelength of 395 nm, emission wavelength of 614 nm, delay time of 1 µs and measurement window 950 µs. The concentration of the single scale inhibitor polymer P1 was measured as seen in FIG. 1 (square, black). The total concentration of three mixed scale inhibitor polymers P1, P2 and P40 (FIG. 1, circle, grey) containing equal concentration of each polymer in the mixture results in an equal time-resolved luminescence signal level at each given concentration. This example shows that single scale inhibitor polymer is measured with efficiency. In FIG. 1: X-axis=polymer concentration (ppm), Y-axis=time-resolved luminescence signal.

Example 2

Total concentration of scale inhibitor polymers are measured in the Example 2.

Experiment set-up was identical to that of Example 1. The total concentration of a mixture of three scale inhibitor polymers P1, P2 and P40 was measured as shown in FIG. 1 (circle, black). The sample containing equal concentration of each scale inhibitor polymer in the mixture resulted in an equal time-resolved luminescence signal level at each given concentration. The example shows that a mixture of scale inhibitor polymers is measured with equal efficiency. In FIG. 1: X-axis=polymer concentration (ppm), Y-axis=time-resolved luminescence signal.

It is apparent to a person skilled in the art that the invention is not limited exclusively to the examples described above, but that the invention can vary within the scope of the claims presented below.

The invention claimed is:

1. A method for determining a scale inhibitor concentration in a sample comprising at least a first scale inhibitor, which is a synthetic organic compound comprising at least one ionised group, the method comprising
optionally diluting and/or purifying the sample,
allowing the at least first scale inhibitor in the sample to interact with a reagent comprising a lanthanide(III) ion,
exciting the sample at a first excitation wavelength and detecting a sample signal deriving from the lanthanide (III) ion at a signal wavelength by using time-resolved luminescence measurement, and
determining the concentration of the at least first scale inhibitor in the sample by using the detected sample signal.

2. The method according to claim 1, wherein the reagent comprising a lanthanide(III) ion is a lanthanide(III) salt or a luminescent lanthanide chelate.

3. The method according to claim 1 wherein the lanthanide(III) ion is selected from europium, terbium, samarium or dysprosium ions, preferably from europium or terbium ions.

4. The method according to claim 1, wherein the concentration of the lanthanide(III) ion in the sample is in the range of 0.01-10 mM, preferably 0.01-1 mM, more preferably 0.01 mM-0.1 mM, even more preferably about 0.01 mM.

5. The method according to claim 1, wherein the scale inhibitor comprises two or more ionised groups, the ionised groups being selected from phosphates, phosphonates, carboxylates, sulphonates, and/or amines, preferably from carboxylates, sulphonates and/or amines.

6. The method according to claim 5, wherein the scale inhibitor is selected from the group consisting of polyelectrolyte compounds comprising carboxylate and/or phosphonate groups; homopolymers and copolymers of ethylenically unsaturated acid monomers; organophosphonates; and combinations thereof.

7. The method according to claim 1, wherein the concentration of the scale inhibitor in the sample is in the range of 0.5-200 ppm, preferably 1-50 ppm, more preferably 1-10 ppm.

8. The method according to claim 1, wherein the sample comprises two or more scale inhibitors, whereby the detected sample signal deriving from the lanthanide(III) ion at the signal wavelength by using time-resolved luminescence measurement corresponds to the total concentration of the two or more scale inhibitors in the sample.

9. The method according to claim 1, wherein the sample comprises a second scale inhibitor, optionally a plurality of successive scale inhibitors, and the individual concentrations of each scale inhibitor in the sample are determined.

10. The method according to claim 9, wherein the concentration of the second scale inhibitor, or any successive scale inhibitor, is determined by using luminescence, time-resolved luminescence, direct fluorescence, absorbance, spectrophotometry, optical rotation measurement, photon counting, inductively coupled plasma (IPC), high-performance liquid chromatography (HPLC), liquid chromatography-mass spectrometry (LC-MS), size exclusion chromatography, colorimetric methods, NMR, or a combination thereof.

11. The method according to claim 9 wherein the concentration of the second scale inhibitor is determined by exciting the sample at a second excitation wavelength and detecting a second sample signal deriving from the lanthanide(III) ion by using time-resolved luminescence measurement.

12. The method according to claim 11, wherein the difference between the first excitation wavelength and second excitation wavelength is at least 10 nm, preferably at least 20 nm, more preferably at least 25 nm.

13. The method according to claim 1, wherein the method includes adding a signal modifier comprising a metal ion, to the sample before the excitation of the sample.

14. The method according to claim 13, wherein the signal modifier comprises a metal ion which is selected from the group consisting of copper, nickel, chromium, iron, gold, silver, cobalt, and any of their mixtures.

15. The method according to claim 1, wherein the time-resolved luminescence measurement is time-resolved fluorescence measurement.

16. The method according to claim 1, wherein the sample is purified by using a purification method selected from centrifugation, size exclusion chromatography, cleaning with solid-phase extraction (SPE) cartridges, dialysis techniques, extraction methods for removing hydrocarbons, filtration, microfiltration, ultrafiltration, nanofiltration, membrane centrifugation and any combinations thereof.

17. The method according to claim 1, wherein a pH value of the sample is adjusted to a level in the range between pH 3 and pH 8, preferably in the range from pH 5 to pH 8.

18. The method according to claim 1, wherein the sample originates from an oilfield or an oil well or from an oil production process.

* * * * *